United States Patent [19]

Cole et al.

[11] 4,407,943

[45] Oct. 4, 1983

[54] IMMOBILIZED ANTIBODY OR ANTIGEN FOR IMMUNOASSAY

[75] Inventors: Francis X. Cole, Stow; Deborah M. Van Voorhis, Watertown, both of Mass.

[73] Assignee: Millipore Corporation, Bedford, Mass.

[21] Appl. No.: 129,671

[22] Filed: Mar. 13, 1980

Related U.S. Application Data

[63] Continuation of Ser. No. 15,724, Feb. 27, 1979, abandoned, which is a continuation of Ser. No. 924,561, Jul. 14, 1978, abandoned, which is a continuation of Ser. No. 751,099, Dec. 16, 1976, abandoned.

[51] Int. Cl.³ ............... G01N 33/54; C12Q 1/04; C12N 11/02
[52] U.S. Cl. ............................ 435/7; 435/34; 435/177; 435/179; 435/180; 436/528; 436/530; 436/809; 436/811
[58] Field of Search ............ 435/7, 34, 174, 177, 435/179, 180, 287; 424/12; 23/230 B, 253 R; 436/528, 529, 530, 531, 811, 809

[56] References Cited

U.S. PATENT DOCUMENTS

| | | | |
|---|---|---|---|
| 3,770,380 | 11/1973 | Smith | 23/230 B |
| 3,839,153 | 10/1974 | Schuurs et al. | 435/7 |
| 3,951,748 | 4/1976 | Devlin | 435/7 |
| 4,002,532 | 1/1977 | Weltman et al. | 435/7 |
| 4,036,946 | 7/1977 | Kleinerman | 23/230 B X |
| 4,039,652 | 8/1977 | Adams et al. | 23/230 B X |
| 4,066,512 | 1/1978 | Lai et al. | 435/177 X |
| 4,111,754 | 9/1978 | Park | 435/7 X |
| 4,200,690 | 4/1980 | Root et al. | 435/7 |

OTHER PUBLICATIONS

Toussaint A. J., Improvement of the Soluble Fluoresant-Antibody Procedure, Experimental Parasitology, vol. 19, 1966, (pp. 71–76).

Toussaint et al. Soluble Antigen Fluorescent-Antibody Technique, Applied Microbiology, vol. 13, No. 4, 1965 (pp. 552–558).

*Primary Examiner*—David M. Naff
*Attorney, Agent, or Firm*—David Prashker; Paul J. Cook

[57] ABSTRACT

An antigen or antibody and an immunochemically neutral protein are immobilized in two stages on a microporous membrane coated with a protein such as zein or collagen. Immobilized antigen to *Toxoplasma gondii* is used in an immunoassay to detect the presence of antibody to *Toxoplasma gondii* in serum. Antibody that becomes bound to the immobilized antigen is detected with an antibody-enzyme conjugate. Immobilizing the immunochemically netural protein on the membrane in a second stage immobilization step minimizes nonspecific binding during the immunoassay.

6 Claims, 4 Drawing Figures

IMMOBILIZED ANTIBODY OR ANTIGEN FOR IMMUNOASSAY

RELATED APPLICATION

This application is a continuation of Ser. No. 15,724, filed Feb. 27, 1979, which was a continuation of Ser. No. 924,561, filed July 14, 1978, which was a continuation of Ser. No. 751,099, filed Dec. 16, 1976. All of these application are now abandoned.

This invention makes use of the immobilization techniques that are disclosed and claimed in the copending, commonly assigned patent application of C. J. Lai et al, Ser. No. 684,746, and now U.S. Pat. No. 4,066,512, granted Jan. 3, 1978, and now published as German OS No. 2,539,657.

FIELD OF INVENTION

This invention relates to the detection of antigen or antibody using immunochemical reactions. Samples of bodily fluid may be tested for the presence of a particular antigen or antibody, from which a diagnostic inference may be made.

BACKGROUND

An immunochemical reaction is here defined as the specific binding which takes place between an antigen and antibody. Antigens and antibodies are components of the immunity system whereby mammals including man protect themselves against infectious agents. An antigen is any substance foreign to the organism into which it has been introduced, which is capable of eliciting the protective immune response of that organism. Most antigens are proteinaceous materials in whole or in part, having high molecular weights. Antibodies are also proteinaceous macromolecules, elicited in response to the presence of a foreign antigen, in the organism. Antibodies have the property of being capable of binding with antigen molecules in highly specific combinations. The binding is characterized by its high degree of specificity and low dissociation constant.

Normally, an animal has only those antibodies which are specifically directed against antigens to which it has been exposed in its environment. However, an animal can be induced to form antibodies against other antigens by artifically introducing them, for example by injection. Medical use is made of this phenomenon to immunize people against disease. It is also possible to cause a laboratory animal such as a rabbit or goat to make antibodies against specific substances. Such antibodies may be obtained from the blood of the animal and are exploited in highly specific assay techniques for the detection of the original antigenic substance. Virtually any protein can in principle be detected by means of an immunochemical reaction.

Immunochemical reactions have been exploited in a variety of ways: for the diagnosis of disease: for the identification of a specific infecting organism, as highly specific enzyme inhibitors, to determine the location of specific proteins in tissues and within cells, and for the quantitative measurement of specific proteins for which no chemical test is available. Since the reaction is a binding of one component (antigen) to another (antibody), there is no net change in the number of reactive groups as in an ordinary chemical reaction. Analysis of an immunochemical reaction therefore requires techniques for differentiating between bound and unbound components.

A variety of methods has been employed in the prior art for the measurement of immunochemical reactions. These include hemagglutination, latex particle agglutination, agar gel diffusion, complement fixation, counterelectrophoresis, and the use of antibodies tagged with fluorescent dyes or radioisotopes.

Hemagglutination and fluorescent antibody techniques have been applied in the detection of antibodies against *Toxoplasma gondii*. Toxoplasma is a protozoan parasite of man which lives primarily inside the cells of the host, so that the organism is difficult to detect by microscopic means. The vast majority of Toxoplasma infections are asymptomatic. However, an asymptomatically infected mother can pass the organism to the fetus, where Toxoplasma infection can cause a variety of birth defects: malformations, hydrocephalus, mental retardation, eye diseases often leading to blindness, and infant mortality. A simple, inexpensive screening test for pregnant mothers would be highly disirable as a step toward the eradication of congenital Toxoplasmosis. Although hemagglutination and fluorescent antibody techniques have been used in the diagnosis of Toxoplasma infection, the standard method has been the dye test. Serum antibody against Toxoplasma is detected in the dye test by taking advantage of the fact that live Toxoplasma cells are partially lysed in the presence of antibody. Lysed cells are distinguishable from unlysed cells by the addition of methylene blue which only stains intact organisms. In practice the test is complicated by the additional requirement for an accessory factor, thought to be complement, which must be obtained from the serum of Toxoplasma-free donors. Great attention to detail is required in carrying out the tests successfully. More significantly, the test is dangerous to laboratory workers since it involves the use of live Toxoplasma. A number of laboratory infections have resulted in individuals who have performed the test (see Jacobs, L., "Serodiagnosis of Toxoplasmosis", in *Immunology of Parasitic Infections*, S. Cohen and E. Sadun, eds., Blackwell Scientific Publications, 1976). An improved immunochemical method for detecting Toxoplasma infection is therefore highly desireable.

Although immunochemical methods generally used in the prior art can be highly sensitive, especially radioimmunoassay using radioisotopetagged antibody, the widespread usefulness of immunochemical assays has been limited by three factors:

(1) the need for a convenient and inexpensive method of separating bound immunochemically reacted components from unbound components, (2) the need for a convenient and inexpensive way to measure the amount of immunochemical reactant bound, and (3) the need for a procedure that can be carried out rapidly.

The first two of these difficulties have been overcome by recent advances in the prior art, the third is overcome by the present invention.

The first of these recent advances in the prior art is the development of techniques for coupling an immunochemically reactive antigen or antibody to an insoluble carrier material. An antibody immobilized on an insoluble carrier can, when exposed to a solution containing antigen, bind the antigen and render it, in turn, immobilized. The entire immunochemical reaction occurs on the carrier and the components which are bound on the carrier can be separated from the unreacted components by conventional techniques for separating solid phase materials from a liquid phase. For example, if the carrier is in the form of beads or finely divided powder, separation can be accomplished by centrifugation or decantation. Alternatively, the immobilized phase may be the inner surface of the reaction vessel itself, or it may be in the form of a sponge or porous matrix, so that separation may be carried out be simple decantation or by removal of the carrier, respectively.

The second advance has been the introduction of an enzyme-tagged antibody, which is a covalent conjugate of an antibody and an enzyme. Each retains its characteristic reactive properties: the antibody remains immunologically reactive and the enzyme retains its catalytic activity. When such a conjugate binds to an immobilized antigen, its presence can be detected through the activity of the coupled enzyme, after separating unbound conjugate by appropriate means.

These two techniques have been used in combination to develop a very sensitive type of assay termed an enzyme-linked immunosorbent assay. The invention which is the subject of this report embodies these basic techniques. For convenience, two types of enzyme-linked immunosorbent assay will be discussed and referred to as EL-1 and EL-2; see the diagram below:

EL-1: C—Ab—Ag—Ab-Enz

EL-2: C—Ag—Ab—AntiAb-Enz

C stands for an inert, insoluble carrier;
Ab symbolizes antibody;
Ag symbolizes antigen;
C—Ab symbolizes carrier-bound antibody;
C—Ag symbolizes carrier-bound antigen;
Ab-Enz symbolizes the conjugate of an antibody with an enzyme;
AntiAb-Enz symbolizes an antibody against immunoglobulin, conjugated with an enzyme.

EL-1 is a technique for detecting the presence of an antigen. Antibody against the antigen is immobilized on an insoluble carrier. The immobilized antibody is then exposed to an antigen-containing fluid. The immobilized antibody harvests the antigen from the solution by binding it in place. The carrier is then separated from the solution, washed free of contaminants, and exposed to a solution of the antibody conjugated to an enzyme. The principle of operation is that the conjugate is able to bind only at sites occupied by the antigen, and that the number of sites so occupied determines the amount of conjugate which can bind. Each site where antigen is bound is thus tagged with bound enzyme whose presence is manifested by its ability to catalyze a reaction. The rate of such reaction is proportional to the amount of enzyme present and becomes a direct measure of the amount of antigen bound.

In EL-2, the component to be detected is an antibody. Antigen is immobilized on the carrier. Binding of the antibody is then measured by the subsequent binding of an anti-immunoglobulin-enzyme conjugate. (See Wisdom, G. B., in Clinical Chemistry, Vol. 22, p. 1243 (1976).)

Antigen or antibody molecules may be immobilized on a solid carrier by a variety of methods known in the art, including covalent coupling, direct adsorption, physical entrapment and attachment to a protein-coated surface. For references describing this methodology, see Silman, I. H. and Katchalski, E. in *Annual Review of Biochemistry*, Vol. 35, p. 873 (1966); Melrose, G. J. H., in *Review of Pure and Applied Chemistry*, Vol. 21, p. 83, (1971); and Cuatrecasas, P. and Anfinsen, C. B., in *Methods in Enzymology*, Vol. 22, (1971).

The method of attachment to a protein-coated surface is disclosed by Lai et al. (German OS No. 2,539,657, U.S. Pat. No. 4,066,512). In this method, the internal and external surfaces of a microporous membrane are first coated with a water-insoluble protein such as zein, collagen, fibrinogen, keratin, glutelin, polyisoleucine, polytryptophan, polyphenylalanine, polytyrosine, or copolymers of leucine with p-amino phenylalanine. Such a coating renders the membrane capable of immobilizing a wide variety of biologically active proteins including enzymes, antigens, and antibodies. A microporous structure is defined as one having more than 50% of its total volume in the form of pores ranging in size from 25 nanometers to 25 micrometers, preferably from 25 nanometers to 14 micrometers. A pore size range from 25 nanometers to 5 micrometers is employed in most applications herein. Uncoated microporous membranes have as much as 70 to 75% of their volume as pore space. The pores permit liquid flow through the membrane. After being coated by zein, for example, the pore space is reduced 5 to 10% with the result that the structure retains its essential properties of having a high proportion of its volume as pore space and permitting liquid flow through the pores. The structure has a large surface area in contact with any solution contained within the pores.

Such a coated membrane, having immobilized antigen or antibody, provides a compact, easy to manipulate carrier for the immobilized antigen or antibody. Its integral structure permits removal of bound from unbound components by simple mechanical means.

A difficulty attending the use of microporous membranes as carriers for immobilized antigen or antibody is that these structures may adsorb proteins nonspecifically. Uncoated membranes of cellulose acetate and nitrate mixed esters can bind certain proteins and are also capable of exchanging bound for soluble protein. The physico-chemical basis for the binding is unclear. Certain proteins appear to bind more readily than others. As a result, assays based on binding a specific antigen, antibody or conjugate in the presence of a mixture of proteins can result in high background interference which may occur in an unpredictable manner.

A related difficulty is presented when coated membranes are used. Coated membranes, as disclosed by Lai, et al, are capable of binding proteins generally, but the binding is neither as selective nor as variable as that displayed by uncoated membranes. Consequently, the use of such membranes to immobilize antibody or antigen in an EL-1 or EL-2 assay may also result in high background interference due to the binding of unwanted protein species. These difficulties have been effectively surmounted by the present invention.

SUMMARY OF THE INVENTION

The present invention is a diagnostic assay method and relates to the materials necessary to practice the method as well as to the method itself. The method is applicable to the detection of an antigen or an antibody in a fluid sample. In one application of the invention, for example, it is used to detect the presence or absence of an antibody in a sample of serum. In another application, an antigen is detected in a sample of a bodily fluid.

The materials used for the practice of the invention include an antigen or antibody immobilized on the surface of an integral structure having a large surface available for contact with the sample and treated to minimize nonspecific protein binding, means for mounting the structure so that sample, wash solutions and reagent may be permitted to flow through the structure, a first reagent comprising a conjugate of an antibody with an enzyme and a second reagent comprising a substrate for the enzyme.

In the preferred embodiment, one component of the immunochemical reaction, either antigen or antibody, is immobilized on the zein-coated internal and external surfaces of a microporous membrane, as previously defined, whereby these surfaces are rendered immunochemically reactive. The membrane is mounted so that the fluid to be tested, for example, serum, may be applied to one side of the membrane, allowed to flow through the pores of the membrane and collected from the other side. The desired immunochemical reaction between a component in the serum and the immobilized component takes place during the period of time in which the serum is in contact with the reactive surfaces during passage through the membrane.

Once the desired immunochemical component is harvested from the test fluid, its presence on the membrane surface may be detected by the subsequent passage through the membrane of an antibody-enzyme conjugate. The antibody moiety of the conjugate is specific for the component to be detected, while the enzyme is chosen to be one whose activity is readily detected by methods well known in the art. Peroxidase is preferred. Immunochemical binding of the conjugate to the harvested component occurs during passage of conjugate solution through the membrane. The conjugate will be immunochemically bound only at sites where the component to be detected is bound.

A reagent solution containing substrate for the bound enzyme is next passed through the membrane. Qualitatively, the presence of immunochemically bound peroxidase is detected by the use of a chromagenic substrate and the subsequent development of color. In the absence of nonspecific binding any color which develops is due to the immunochemical binding of the conjugate, which in turn depends on the presence of the component to be detected and demonstrates the existence of the component to be detected in the test fluid.

Quantitatively, the amount of color which is developed may be measured, for example, by spectrophotometry. The amount of color developed is a measure of the amount of chromagenic substrate converted to product, which in turn is a measure of the amount of enzyme bound. In the absence of nonspecific binding of the conjugate, the amount of conjugate bound is a measure of the amount of the component to be tested harvested on the membrane, and hence a measure of the amount of the component present in the test fluid.

In practice, a certain amount of nonspecific binding occurs. It is therefore necessary to employ a control sample, in which it is known that the component to be detected is absent. An important feature of the invention is the adoption of techniques which minimize the amount of nonspecific binding and maximize the differences observed between positive samples and controls. In this regard, the use of a zein coating on the microporous membranes, the use of a two stage immobilization procedure, and the use of highly purified peroxidase in forming the conjugate have been effectively combined in the preferred embodiment to reduce nonspecific binding. The procedures employed are critical to the practice of the invention and will be discussed in detail below.

It has been discovered that immunochemical assays may be carried out according to the invention using extremely short incubation times. Complete tests can be run from start to finish in 20-30 minutes, as compared to several hours for prior methods. In addition, the invention provides advantages of simplicity and ease of operation, adaptability for routine use, and lack of requirement for a highly trained technician or expensive equipment. Because of these advantages, the invention renders immunochemical assays more readily available for use in a wide range of clinical, industrial, and environmental tests. Examples of the invention's applicability include the routine detection of hepatitis B antigen in donated blood, the diagnosis of Toxoplasmosis, and the testing of foodstuffs for microbial contamination or toxins.

DETAILED DESCRIPTION OF THE INVENTION

Figure 1:
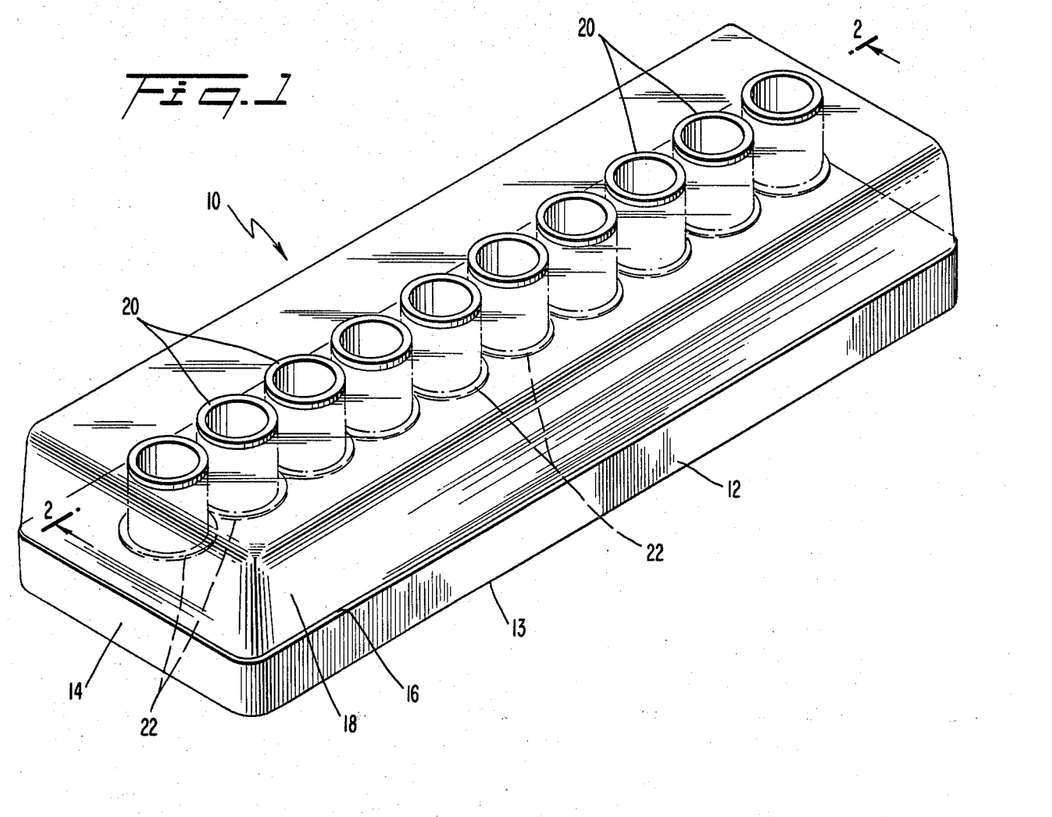
FIG. 1 is a perspective view of a device for use in the diagnostic assay of multiple samples, constructed in accordance with one embodiment of the invention.
Figure 2:
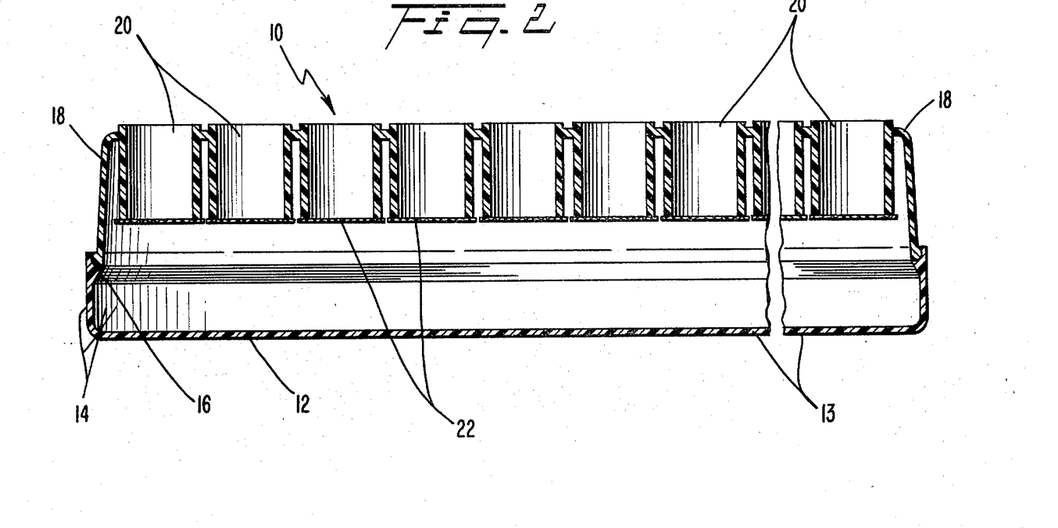
FIG. 2 is a fragmentary section, taken on the line 2—2 of FIG. 1, looking in the direction of the arrows.
Figure 3:
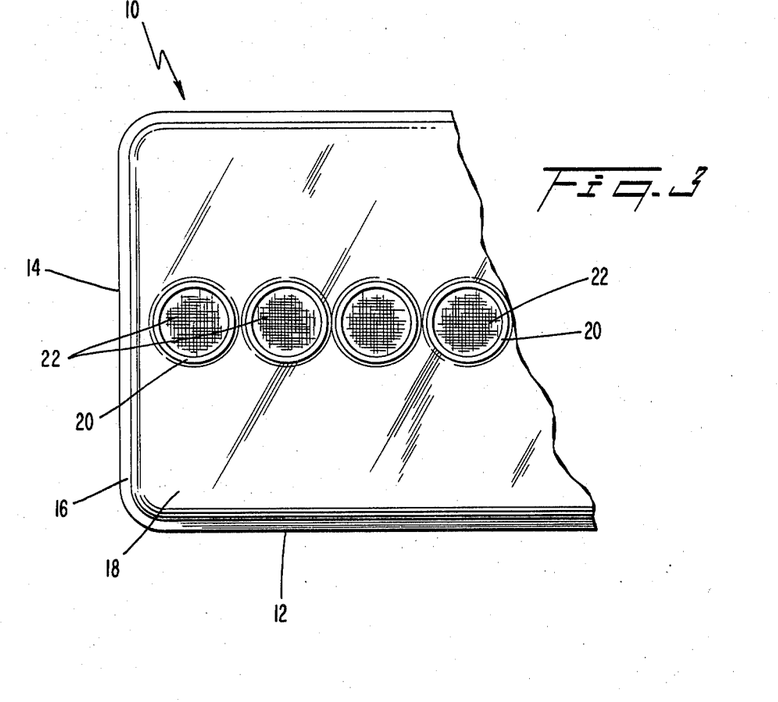
FIG. 3 is a fragmentary top plan view thereof.
Figure 4:
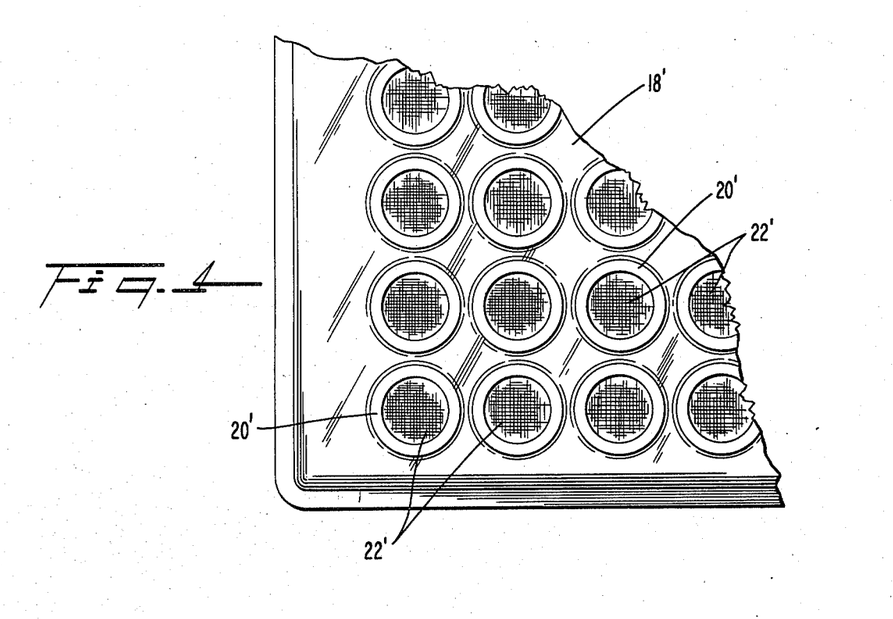
FIG. 4 is a fragmentary top plan view of a device made in accordance with a different embodiment of the invention.

Proper function of the invention is in part dependent upon the choice of a suitable surface upon which antigen or antibody is immobilized. The surface structure should permit fluid flow into and through the structure and should present a large surface area relative to the volume of fluid contained within the structure. Such requirements are satisfied, to varying degrees, by such diverse structures as hollow fiber bundles, porous refractory filters, microporous membrane filters, and packed columns. The choice of support in each case will depend upon the type of assay and the use to which it is put. For a wide variety of assays, where speed, convenience and economy must be considered, the use of a microporous membrane is preferred.

The method of immobilizing antigen or antibody to the surface of such a structure may in principle be any method suitable for the particular surface employed and material to be attached. The method of Lai, supra, is suitable for immobilization of biologically active materials to a wide variety of surfaces. In addition, the use of a coating has the unexpected advantage of providing a means for controlling nonspecific protein binding.

In the preferred embodiment, zein-coated microporous membranes are employed. The term microporous membrane is here defined as having pores that fall within the size range from 25 nanometers to about 25 micrometers and preferably, from 25 nanometers to 14 micrometers. The coating may be applied without substantial loss of flow-through capability and with only a slight diminution of pore volume. Microporous membrane filters present the further advantage that their external as well as their internal surfaces become coated and thus able to immobilize antibody. Particulate antigens, such as whole cells or cell fragments, can be bound even though they may be too large to enter the pores of the membrane. Preparations of antibody immobilized to zein-coated microporous membrane filters remain immunochemically reactive for long periods of time under proper conditions. Samples may be stored under refrigeration or lyophilized and stored in a controlled humidity environment.

Antigens and antibodies used in the invention may be prepared by standard techniques well known in the art. Antibodies may be prepared from the serum of animals such as rabbits, horses, or goats which have been immunized against the appropriate antigen. Antigens are purified from the source organism by known techniques used in the separation and purification of biological materials.

Since the structure having the immobilized component is to be exposed to a bodily fluid comprising a mixture of proteinaceous materials, any affinity between such materials and the structure's surface can result in nonspecific binding. Such binding could seriously interfere with the assay. For example, the total amount of protein which could bind to the uncoated surfaces of a microporous membrane could exceed the amount bound by a specific immunochemical reaction. Similarly, where a coated microporous membrane is employed, the membrane may retain the ability to bind additional protein nonspecifically.

It has been discovered as a part of this invention that nonspecific binding may be minimized by interposing a second stage immobilization step, in which an immunochemically neutral protein is immobilized to the filter. Immobilization therefore occurs in two stages according to the preferred embodiment of the invention: a first stage in which the desired immunochemical component is immobilized, and a second stage, following the completion of the first, in which an immunochemically neutral protein such as fetal calf serum or bovine gamma globulin is next immobilized. The term immunochemically neutral is defined in terms of the specific components of the assay. Any protein which does not combine immunochemically with a component of the assay or with one of the reagents is considered immunochemically neutral, even though such protein might be immunochemically reactive in another system. The combination of coating a microporous membrane by the method of Lai, immobilizing an immunochemical reactant in a first immobilization step, followed by immobilizing an immunochemically neutral protein in a second immobilization step results is substantial reduction of nonspecific binding when the membrane bearing its immobilized components is exposed to a mixture of proteinaceous materials.

The conjugate of antibody with enzyme is made using techniques known in the prior art. (For references, see Avrameas, S. and Uriel, J., in Comptes Rendus Hebdomadaires des Seances de l'Academie des Sciences, vol. 262, p. 2543, (1966); Nakane, P.K. and Pierce, G.B., in Journal of Histochemistry and Cytochemistry, vol. 14, p. 929, (1966); Nakane, P.K., in Methods in Enzymology, vol. 37, p. 133, (1975).) In an EL-1 type of assay, the antibody moiety of the conjugate should have the same immunological specificity as the immobilized antibody. In EL-2 where the substance to be detected is an antibody, the immunochemically reactive moiety of the conjugate must be an antibody capable of binding immunochemically with the antibody to be tested. Such antibodies may be obtained by immunizing an animal with the antibody or immunoglobulin fraction of serum from the animal in which the antibody to be tested originated. For example, where the antibody to be tested is a human antibody, a goat antibody against human antibody is obtained from the serum of a goat immunized against human immunoglobulin (antibody). The enzyme moiety may be any enzyme capable of catalyzing a reaction which can be detected by any method known to those skilled in the art, and which retains its activity after conjugation with antibody. Horseradish peroxidase is preferred because of its convenience and suitability to a wide range of applications. It is well known that the enzyme catalyzes the oxidation of a variety of organic compounds in the presence of hydrogen peroxide. Many such organic substrates are chromagenic, i.e., undergo a color change upon oxidation.

It has been found in the present invention that the purity of the enzyme preparation used in the formation of conjugate has an effect on the degree of nonspecific binding. The greater the purity of the enzyme preparation, the less the nonspecific binding. In part, the reduction is made possible because, the total amount of conjugate protein required is reduced as the specific activity of the enzyme is increased. The opportunity for nonspecific binding is therefore reduced as well. In the preferred embodiment, the use of a highly purified peroxidase preparation has been found to significantly reduce the amount of color reaction observed in control samples as compared with known positives.

The first reaction step in the assay procedure involves bringing together the immobilized component of the immunochemical reaction and the test fluid, which may contain the component to be detected, such that reactive contact occurs. It is at this step that the choice of a suitable carrier for the immobilized component, having a large surface area in relation to the volume contained within the structure becomes important. As the test fluid flows through the structure, the probability that a solute molecule will contact one of the surfaces during liquid flow through the structure is very high. The probability of an immunochemically reactive contact is further increased as the probability of such collisions per unit of surface area is maximized. It is believed that the probability of such collisions depends, in a general way, upon the parameters of pore size and flow rate, where solute concentration and reaction temperature are held constant. Thus, the more constricted the passageway through which the solute molecules pass, relative to their mean free path, the greater the likelihood of collision with the surface. The lower the flow rate, the longer the residence time of the solute within the structure itself, and the greater the probability of collision. In accord with the foregoing considerations, structures having large ratios of surface exposed to the volume of fluid flowing therethrough are employed in the present invention in an attempt to increase the probability of reactive contact with the surface and to reduce the time required to carry out the reactions involved.

A test kit for diagnostic detection of an immunochemically reactive substance in a test fluid is provided which comprises a plate formed with a plurality of recessed portions that are spaced from each other. Each recessed portion is bounded by a side wall and each recessed portion is formed with a downwardly directed opening. A microporous membrane is sealed across each said opening, each of these membranes having internal and external surfaces and an interconnecting network of pores extending throughout its thickness which permits fluid to flow therethrough. In this manner, the internal and external surface areas are exposed to any fluid flowing through the membrane, the aggregate internal surface area of the membrane being many times larger than the external surface area. The membrane may have a coating comprising a protein selected from the group consisting of zein and collagen. Each membrane has immobilized on its coated external surfaces a substance selected from the group consisting of antigens and antibodies, one of which is capable of reacting immunochemically with the composition to be detected. Thus, when the test fluid is placed within the compartment and flows through the membrane, a reactive contact between the composition in the test fluid and the substance immobilized on the membrane surfaces will occur. A reagent mixture comprising the conjugate of an antibody and an enzyme is then added to the membrane. The antibody moiety is capable of immunochemically reacting with the substance to be detected and the enzyme moiety is capable of catalyzing a measurable reaction in the presence of chromogenic substrate.

A test kit for diagnostic detection of an antibody of *Toxoplasma bondii* in serum thus comprises a support member having a plurality of compartments each having a top opening, a nonporous side wall and a floor. A plurality of coated, microporous membranes are mounted in separate compartments of the support and form the floor thereof, each membrane having an interconnecting network of pores extending throughout its thickness which permits fluid to flow therethrough. In this manner, the internal and external surface areas are exposed to any fluid flowing through the membrane, the aggregate internal surface area of the membrane being many times larger than the external surface area. Each membrane preferably has a coating comprising a protein selected from the group zein and collagen. The membrane has immobilized on its coated surfaces a first substance comprising an antigen of *Toxoplasma gondii*, and a second, separately immobilized substance selected from the group consisting of proteins which are immunochemically neutral in the diagnostic test. When serum is placed within the compartment and flows through the membrane, a reactive contact with the antibody of *Toxoplasma gondii* occurs while nonspecific binding is suppressed.

The dry reagents comprise the following: the conjugate of an antibody and peroxidase, the antibody moiety being capable of immunochemically reacting with an antibody of *Toxoplasma gondii;* a dry buffer mixture comprising preweighted compounds of a buffer suitable as dilutent; and as a reagent solvent, a peroxidase substrate mixture in preweighed dry powder form comprising 4-amino antipyrine, 4-hydroxybenzoate, lyophilized glucose oxidase, glucose and buffer salts all in appropriate proportions. The addition of a prescribed volume of water is sufficient to dissolve the mixture and render the mixture ready for use. The positive control comprises a lyophilized sample of serum containing antibody to *Toxoplasma gondii,* and the negative control comprises a lyophilized sample of serum lacking an antibody to *Toxoplasma gondii.*

Referring now in detail to the drawings by numerals of reference, the device 10 is formed from a molded plastic, preferably transparent and tough, base on a tray 12. The tray 12 has a bottom panel 13 and upstanding walls 14 that are formed with an internal lip 16. A holder 18 is detachably seated on the lip 16. This holder is also formed from tough, transparent plastic and it in turn is formed with a plurality of generally cylindrical, cup-like recessed parts 20. The bottom opening of each cup 20 is covered with a membrane 22 that is heat sealed to the lower rim of the cup. In the embodiment of the invention shown in FIG. 4, the holder 18' is formed with a much larger number of cups 20', thus permitting a single device to be used for a larger number of assays.

In use, a sample is poured into a cup. The sample flows through the membrane into the tray. As will be described in detail hereafter, the membrane is washed and treated with reagents, as needed, to detect the presence or absence of a particular material in the sample.

In the preferred embodiment, microporous membranes are employed as carrier for the immobilized component. The membrane is mounted in a convenient holder in order to permit fluid flow of sample, wash solutions and reagents through the pores of the membrane. Such membranes are available in a variety of pore sizes. The optimum pore size will depend on the requirements of the specific assay, including the flow characteristics of the sample to be tested and the amount of fluid to be processed. The incubation time is governed by the flow rate through the filter and may be controlled by a variety of means known in the art. A simple and effective technique is to apply fluid dropwise to the upper surface of the membrane so that the rate of flow of fluid is governed only by the hydrostatic pressure exerted by the drop as its rests on top of the membrane. If the droplet is small enough, i.e., approaching the retention volume of the membrane, the fluid will tend to flow into the pores of the membrane and be retained there by capillary attraction until displaced by additional fluid. Reaction time under these circumstances is controlled by the residence time of the sample within the membrane pores.

When the structure is mounted so that reactants and reagents can flow through the structure from one side to the other, the entire sequence of steps is easily and rapidly performed. First, test fluid is permitted to flow through the structure in order to harvest any of the component to be tested present therein. Second, a solution of conjugate is permitted to flow through at a controlled rate so that conjugate may immunochemically bind to any component to be tested harvested in the first step. Third, substrate solution is permitted to flow through the structure at a controlled rate, in order to permit immunochemically bound enzyme to convert the substrate to a measureable product. Washing steps may be interposed between the three reaction steps if desired. The incubation temperature may be controlled within the range of 15° C. to 45° C. to suit individual needs. Room temperature is preferred for the sake of convenience, in a qualitative assay. In the practice of the preferred embodiment, using Toxoplasma antigen immobilized on a microporous membrane, the presence of antibody to Toxoplasma in serum is readily detected using a series of 5 minute incubations for each step with a washing step interposed between each, so that the entire sequence of reactions is completed in 20–30 minutes, as described in detail in Example 1.

There is a variety of chromagenic substrates available for the detection of peroxidase activity. For qualitative tests, it is desirable to employ either a chromagen which precipitates on the membrane when acted upon by peroxidase, or one in which the peroxidase reaction product binds preferentially to the membrane. An example of the former is 3-aminoethylcarbazole. An example of the latter is 4-amino antipyrine. Quantitative measurements may be carried out using a soluble chromagen product and measuring the development of color by suitable methods such as spectrophotometry.

The speed and operating convenience of the present invention make it eminently suited for routine analysis. All the components can be provided in a stable form, dried or lyophilized, so that a technician has only to dissolve the preweighed mixture of buffer salts or reagents in a predetermined amount of water prior to use. A test kit embodying these advantages is contemplated. For example, a test kit for the detection of Toxoplasma antibodies in serum would comprise the following: microporous membranes having Toxoplasma antigen immobilized thereon mounted in a suitable holder for adding reaction components to the upper surface of the membrane and for collecting the materials from the under surface which have flowed through, lyophilized antibody-enzyme conjugate, dried buffer salts preweighed, and dry substrate preweighed. Where the enzyme moiety of the conjugate is peroxidase, a substrate mixture containing 4-amino antipyrine, 4-hydroxybenzoate, lyophilized glucose oxidase, glucose and buffer salts is advantageous. The action of glucose oxidase on glucose generates the hydrogen peroxide substrate used in the peroxidase reaction, thereby eliminating the need to provide hydrogen peroxide, which is difficult to stabilize for long periods of storage. When oxidized by peroxide in the presence of peroxidase, 4-amino antipyrine forms a colored substance which preferentially adsorbs to the microporous membrane. In this manner, all of the components of the test can be provided in stable, dry, water soluble form.

The described invention presents significant advances over the prior art in terms of speed, operating simplicity, convenience and expense. Specific examples of procedures embodying aspects of the invention will next be presented, in order to further demonstrate the invention.

EXAMPLE 1—TOXOPLASMA ANTIBODY SCREENING ASSAY

A. A microporous membrane filter having 3 micron nominal pore size (Type SS, manufactured by Millipore Filter Corp., Bedford, Mass.) was coated with zein according to the following procedure. Zein (79 g) was dissolved in a solvent mixture containing 180 ml ethanol, 340 ml n-butanol. 80 ml water and 30 ml cellosolve, by mixing in a ball mill until completely dissolved. Filters were submerged in the zein solution, allowed to soak for 16 hours, removed and air dried.

B. Toxoplasma antigen was immobilized on coated membrane filters by immersing the coated filters overnight at 4° C. in 1.5 m. of an antigen preparation containing 6 mg–12 mg total protein. The filters were then air dried at room temperature, washed with MilliRO TM (Registered Trade mark of Millipore Corporation, Bedford, Mass.) water and again air dried at room temperature.

The Toxoplasma antigen preparation was a lysate of fresh Toxoplasma cells obtained from peritoneal exudates of infected mice by techniques known in the art.

C. The second-stage immobilization was carried out after the immobilization with Toxoplasma antigen was completed and the filters were dry. The filters were placed in a beaker containing a solution of bovine gamma globulin fraction II at a concentration of 20 mg per ml in MilliRO TM water and allowed to soak for approximately 16 hours. The filters were then air dried at room temperature, washed once with MilliRO TM water and air dried again at room temperature.

D. Serum to be tested was obtained from patient's blood samples which were allowed to clot to remove red blood cells and clotting proteins. The serum sample was diluted with an equal volume of tris-saline buffer. (Tris-saline buffer contained 0.1 M 2-amino-2-hydroxymethyl-1,3-propanediol and 0.15 M sodium chloride, pH 8.0).

E. A coated membrane filter having immobilized Toxoplasma antigen was mounted in a suitable holder to permit added fluid to enter one side of the membrane, flow through the membrane pores and exit from the other side of the membrane. Serum (100 $\mu$l, diluted 1:1 in tris-saline buffer) was passed into the membrane's pores and allowed to remain there for 5 minutes at room temperature. Serum was then washed out of the filter by addition of 1 ml tris-saline buffer.

F. The filter was then treated by the addition of 100 $\mu$l of antibody-enzyme conjugate. The conjugate was composed of horseradish peroxidase (Worthington, HPOFF) coupled to goat anti-human IgG antibody (Meloy Laboratories, Inc., Springfield, Va., lot No. G51624, 34.2 mg/ml). Coupling was carried out by the metaperiodate activation method, as described by Nakane, P. K. and Kawaoi, A., in J. Histochem. Cytochem., vol. 22, p. 1084 (1974). The conjugate solution added to the filter had 6.6 $\mu$g/ml total conjugate protein and was diluted 500-fold from a stock solution, using 10% fetal calf serum as diluent. The conjugate was incubated with the filter for 5 minutes, then washed with 1 ml tris-saline buffer. G. Qualitative staining was done using 3-amino-ethylcarbazole as the chromagen. The chromagen (10 mg) was dissolved in 6 ml dimethyl sulfoxide, followed by the further addition of 50 ml 0.02 M sodium acetate pH 5.0. Just before use, 0.5 ml of 3% (v/v) hydrogen peroxide was added. The solution was then allowed to react 5 minutes with the components immobilized on the membrane filter while flowing through the filter. The presence of antibody to Toxoplasma in the test serum was indicated by a red color developed on the test filter. A filter treated with a sample of normal serum remained white or faintly colored.

EXAMPLE 2

In this experiment, the effect of varying the incubation times for the serum incubation step (as described in Example I/E) and for the conjugate incubation step (Example I/F) was tested. The experimental procedure of Example I was followed, except that the second-stage immobilization (step I/C) was omitted. Test samples of serum were known to be negative (lacking Toxoplasma antibody) or positive (containing Toxoplasma antibody) by the fluorescent antibody test. (Kelen, A. E., Ayllon-Leindl, L. and Labzoffsky, M. A., Canad. J. Microbiol., vol. 8, pp 545–554 (1962).

A. The time of serum incubation was varied, while conjugate incubation time and substrate incubation time were held constant. Results are shown in Table 1, where a minus sign (−) indicates lack of color development, and plus signs (+) indicate shades of color on a scale form light pink (+) to dark pink (+++).

TABLE 1

| Tube number | Serum contents | Serum incubation time (minutes) | Result |
|---|---|---|---|
| 1 | negative | 15 | + |
| 2 | negative | 15 | + |
| 3 | positive | 5 | +++ |
| 4 | positive | 5 | +++ |
| 5 | positive | 10 | +++ |
| 6 | positive | 10 | +++ |
| 7 | positive | 15 | +++ |
| 8 | positive | 15 | +++ |

The 5 minute samples developed as much color as the 15 minute samples, indicating that a 5 minute incubation was adequate.

B. In this experiment, serum incubation time and substrate incubation time were held constant at 5 minutes, and conjugate incubation time was varied from 5 minutes to 15 minutes. The results are shown in Table 2.

TABLE 2

| Tube number | Serum contents | Conjugate incubation time (minutes) | Result |
|---|---|---|---|
| 1 | negative | 15 | + |
| 2 | negative | 15 | + |
| 3 | positive | 5 | +++ |
| 4 | positive | 5 | ++ |
| 5 | positive | 10 | +++ |
| 6 | positive | 10 | +++ |
| 7 | positive | 15 | +++ |
| 8 | positive | 15 | +++ |

It was concluded that 5 minutes reaction times were adequate for both the serum incubation and the conjugate incubation.

EXAMPLE 3

This representative experiment was designed to test the effectiveness of the second-stage immobilization, described in Example I/C, in reducing the background color of negative control samples. The serum samples employed were known negative (Toxoplasma antibody absent) or positive (having Toxoplasma antibody) samples as previously determined by the fluorescent antibody test, or the hemagglutination assay. (Jacobs, L. and Lunde, M. N., J. Parasitol, vol. 43, pp 303–314 (1957)). The tests were carried out as described in Example 1, except that for one-step immobilization samples, step I/C was omitted, and for two-step immobilization samples, 100% (W/v) fetal calf serum was substituted for bovine gamma globulin in step I/C. The results are shown in Table 3. The symbols employed have the same meaning as in Example 2.

TABLE 3

| Tube number | Sample | Method of Immobilization | Result |
|---|---|---|---|
| 1 | negative | 1 - step | + |
| 2 | negative | 1 - step | + |
| 3 | negative | 2 - step | − |
| 4 | negative | 2 - step | ± |
| 5 | negative | 2 - step | − |
| 6 | negative | 2 - step | − |
| 7 | positive | 2 - step | +++ |
| 8 | positive | 2 - step | +++ |

It was concluded that 2-step immobilization significantly decreased background color in negative samples, and improved the color differential between negative and positive samples.

GENERAL CONCLUDING REMARKS

The present invention relates to the detection of antigens and antibodies in bodily fluids for diagnostic purposes, exploiting immunochemical reactions. A combination of factors and principles has been brought to bear in reducing the time required to carry out the sequence of steps and in improving the operating simplicity and economy of the entire procedure.

In the preferred embodiment the use of zein or collagen coated microporous membranes provides significant advantages in the practice of the invention. First, immobilization of specific antigens or antibodies is readily effected. Second, the binding properties of coated microporous membranes make then sufficiently manageable that nonspecific binding can be suppressed to an acceptable level.

The method is applicable to any test fluid capable of flowing through the type of structure described, or any fluid capable of being rendered flowable therethrough, by dilution, prefiltration, and the like. The method is suitable for use with either EL-1 or EL-2 assays, i.e., either an antigen or an antibody may be detected in the test fluid. Adaptation of the invention for the assay of a particular antigen or antibody is primarily a matter of choosing the appropriate component to be immobilized on the structure, and choosing the proper immunochemical component to be conjugated to an enzyme.

While the invention has been described in connection with specific embodiments thereof, it will be understood that it is capable of further modifications and this application is intended to cover any variations, uses, or adaptations of the invention following in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of nonimmunochemically immobilizing two proteins on the internal and external surfaces of a microporous membrane having pore sizes in the range from 25 nanometers to 25 micrometers in its uncoated state, comprising:

coating the internal and external surfaces of the membrane with a protein selected from the group consisting of zein and collagen, to provide a coated membrane that is at least 50% microporous, immersing the coated membrane in a solution of a biologically active first protein selected from the group consisting of the antigen of and the antibody to *Toxoplasma gondii*, in order to immobilize the first protein, then immersing the coated membrane having the biologically active first protein immobilized thereon in a solution of an immunochemically neutral second protein selected from the group consisting of fetal calf serum and bovine gamma globulin fraction II, in order to immobilize the second protein while the first protein remains immobilized and retains its biological activity.

2. A method in accordance with claim 1 wherein the first immobilized protein is an antigen.

3. A method in accordance with claim 1 wherein the first immobilized protein is an antibody.

4. In an immunochemical assay for detecting the presence in a solution of an immunochemical component selected from the group consisting of the antigen of and the antibody to *Toxoplasma gondii*, comprising a specific binding reaction between a first immunochemical component selected from the group consisting of said antigen and said antibody immobilized on the coated surfaces of a microporous membrane having pore sizes in the range from 25 nanometers to 25 micrometers in its uncoated state, and that is at least 50% microporous, and a second component selected from the group consisting of the antigen of and the antibody to *Toxoplasma gondii* that binds with the first immunochemical component in a test fluid, wherein nonspecific binding occurs as a side reaction and wherein the coating is a protein selected rom the group consisting of zein and collagen, a method for suppressing the nonspecific binding comprising:

treating the coated membrane, having the first component immobilized thereon, by immobilizing on the coated membrane a protein immunochemically neutral in the assay and selected from the group consisting of fetal calf serum and bovine gamma globulin fraction II, whereby when the second component is brought into reactive proximity to the immobilized first component, a specific immunochemical reaction takes place and nonspecific binding is suppressed.

5. A method in accordance with claim 4 wherein the first component is an antibody and the second component is an antigen.

6. A method in accordance with claim 4 wherein the first component is an antigen and the second component is an antibody.

* * * * *